US00PP31410P2

(12) United States Plant Patent
Keysers

(10) Patent No.: US PP31,410 P2
(45) Date of Patent: Jan. 28, 2020

(54) ***ABELIA* PLANT NAMED 'LITTLE LADY'**

(50) Latin Name: *Abelia grandiflora*
Varietal Denomination: LITTLE LADY

(71) Applicant: Klemens Keysers, Kevelaer (DE)

(72) Inventor: Klemens Keysers, Kevelaer (DE)

( * ) Notice: Subject to any disclaimer, the term of this patent is extended or adjusted under 35 U.S.C. 154(b) by 0 days.

(21) Appl. No.: 15/999,876

(22) Filed: Aug. 23, 2018

(51) Int. Cl.
*A01H 6/00* (2018.01)
*A01H 5/02* (2018.01)

(52) U.S. Cl.
USPC ..... Plt./226

(58) Field of Classification Search
USPC ..... Plt./226
CPC ..... A01H 6/00; A01H 5/02
See application file for complete search history.

(56) References Cited

PUBLICATIONS

UPOV Record Detail Feb. 16, 2017.*

* cited by examiner

*Primary Examiner* — Keith O. Robinson
(74) *Attorney, Agent, or Firm* — Cassandra Bright

(57) ABSTRACT

A new and distinct *Abelia* cultivar named 'LITTLE LADY' is disclosed, characterized by a very compact plant form, and dark pink, flower-like sepals which have ornamental value. The new variety is an *Abelia*, normally produced as an outdoor garden or container plant.

1 Drawing Sheet

Latin name of the genus and species: *Abelia grandiflora*.
Variety denomination: 'LITTLE LADY'.

BACKGROUND OF THE INVENTION

The new *Abelia* cultivar is a product of a chance discovery by the inventor in Kevelaer, Germany. The new variety was discovered as a naturally occurring single branch mutation in nursery during August of 2015.

The parent is *Abelia grandiflora* 'Prostrata', unpatented.

Asexual reproduction of the new cultivar 'LITTLE LADY' was first performed in September of 2015 at a nursery in Kevelaer, Germany. Vegetative soft wood cuttings were used. Subsequently, 3 generations have been reproduced and shown that the unique features of this cultivar are stable and reproduced true to type.

SUMMARY OF THE INVENTION

The cultivar 'LITTLE LADY' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'LITTLE LADY', These characteristics in combination distinguish 'LITTLE LADY' as a new and distinct *Abelia* cultivar:

1. Dark pink, flower-like ornamental sepals.
2. Good container plant.
3. Very compact growth.

PARENT COMPARISON

Plants of the new cultivar 'LITTLE LADY' are similar to plants of the parent in most horticultural characteristics, however, plants of the new cultivar 'LITTLE LADY' differ in the following;

1. Foliage of the new variety is wider and more rounded than foliage of the parent variety.
2. Plants of the new variety are more floriferous than plants of the parent variety.
3. Plants of the new variety produce smaller flowers than plants of the parent variety.
4. Plants of the new variety are snore compact, with shorter branches than the parent.
6. Sepal color of the new variety is green and red with white, sepal color of the seed parent is darker, brown-red.

COMMERCIAL COMPARISON

Plants of the new cultivar 'LITTLE LADY' can be compared to the variety *Abelia* 'Keiser' U.S. Plant Pat. No. 21,632. These varieties are similar in most horticultural characteristics however, 'LITTLE LADY' differs in the following:

1. The new cultivar has lighter, glossier leaves; comparator has darker green leaves.
2. The new variety is more compact than this comparator.

BRIEF DESCRIPTION OF THE PHOTOGRAPH

The accompanying photograph illustrates in full color a typical plant of 'LITTLE LADY' grown in 1-gallon container, at approximately 1 year old. The plant was grown in a poly-house in Grand Haven, Mich. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2015, $6^{th}$ edition, except where general terms of ordinary dictionary significance are used. The following observations and measurements describe 'LITTLE LADY' plants grown in a poly-greenhouse in Grand Haven, Mich. Measurements were taken during August 2018. The plants were about 1 year old in 1-gallon containers. The growing temperature ranged from approximately 18° C. to 27° C. during the day and 5° C. to 10° C. at night. Measurements and numerical values represent averages of typical plant types.

*Botanical classification.*—*Abelia grandiflora* 'LITTLE LADY'.

Propagation:

*Time to initiate roots.*—1 to 2 months at approximately 18 to 27° C.

*Root description.*—Fibrous and fleshy. Thin with moderate density. Freely branching. White to tan in color, not effectively measured with a color chart.

*Time to produce a rooted young plant.*—About 40 days at approximately 18 to 27° C.

Plant:

*Plant type.*—Perennial flowering shrub.

*Age of plant described.*—Approximately 2 to 3 years old.

*Growth habit.*—Upright and outwards, mound shaped.

*Pot size of plant described.*—1-gallon pot.

*Overall plant shape.*—Broad mound.

*Height.*—29 cm.

*Plant spread.*—52 cm.

*Plant vigor.*—Moderate.

*Branching characteristics.*—Basal branching.

*Length of primary lateral branches.*—23 cm.

*Diameter of lateral branches.*—2 mm.

*Quantity of lateral branches.*—28.

*Stem.*—Stem shape: Round. Stem strength: Good. Aspect: 10-90 degrees from center, straight or arching. Color: Greyed-Purple 183B. Texture: Slightly pubescent.

*Internode length.*—2 cm.

*Anthocyanin coloration.*—Absent.

Foliage:

*Leaf.*—Arrangement: Opposite. Leaf shape: Broad elliptic. Average Length: 2.75 cm. Average Width: 1.5 cm. Apex: Acute to acuminate. Base: Obtuse. Margin: Crenate. Texture of top surface: Waxy. Texture of bottom surface: Waxy, protruding midrib. Color: Young foliage upper side: Yellow-Green 146B Young foliage under side: Yellow-Green 146D Mature foliage upper side: Green NN137D. Mature foliage under side: Yellow-Green 148C. Glossiness: Medium. Venation: Color upper side: Yellow-Green 145C. Color under side: Yellow-Green 148C. Petiole: Average Length: 3 mm. Diameter: 1 mm. Texture: Smooth, waxy. Petiole color upper side: Yellow-Green N144C. Petiole color lower side: Yellow-Green N144C.

Flower:

*Natural flowering season.*—Summer.

*Flowering arrangement.*—Single salverform flowers.

*Flowering habit.*—Terminal ends of branches.

*Quantity of flowers per lateral stem.*—About 10.

*Quantity of buds per lateral stem.*—10.

*Quantity of flowers and buds per plant.*—About 50 to 200.

*Flower aspect.*—Upwards and outwards.

*Size.*—Height: 1 cm. Diameter: 1 cm.

*Flower other characteristics.*—Shape: Single whorl with 5 slightly recurved petals. Throat diameter: 5 mm. Flower tube length: 7.5 mm. Flower tube diameter: 2 mm. Persistence: Self-cleaning. Fragrance: Sweet.

*Bud.*—Shape: Linear-spatulate. Length: 1 cm. Diameter: 1 cm. Color: Yellow-Green 154C.

*Petal.*—Petal arrangement: Whorl. Number of petals per flower: 5. Petal Shape: Elliptic-Obovate. Margin: Entire. Tip shape: Obtuse. Length from throat: 7.5 mm. Width: 7.5 mm. Tube length: 7.5 mm. Tube width: 2 mm. Texture: Upper: Smooth. Lower: Smooth. Appearance: Smooth, slightly recurved petals. Throat texture: Smooth. Tube texture: Smooth.

*Color.*—When opening: Upper surface: White NN155D flushed Yellow Green 154C. Under surface: White NN155D flushed Yellow Green 154C. Fully opened: Upper surface: White NN155D. Under surface: White NN155D.

*Flower tube color.*—White NN155D.

*Flower throat color.*—White NN155D.

*Sepal.*—Arrangement: Whorl arrangement. Number: 5. Shape: Elliptic. Tip: Acute. Base: Truncate Margin: Entire. Length: 7.5 mm. Width: 3 mm. Texture, Upper: Smooth. Texture, Lower: Smooth. Other: Sepals darken after corolla falls off. Color: At Maturity: Upper side: Greyed-Red 182B. Under side: Greyed-Red 182B. After corolla falls off Upper side; Greyed-Red 182A. Under side: Greyed-Red 182A. Blotches in flower throat: Absent.

*Peduncle.*—Length: 5 mm. Diameter: 1 mm. Color: Green 143C. Orientation: 45°. Strength: Good. Texture: Smooth.

Reproductive organs:

*Stamens.*—Number: Average 4. Filament length: 1.0 cm. Filament color: White N155D.

*Anthers.*—Shape: Oblong. Length: 2 mm. Color: White N155D. Pollen color: White N155D. Pollen amount: Minimal.

*Pistil.*—Number: 1. Length: 1.0 cm. Style: Length: 1.5 cm. Color: White N155D. Stigma: Shape: Round. Color: Greyed green 197D. Position: Below anthers.

Other characteristics:

*Seeds and fruits.*—Not available at the time of filing.

*Disease/pest resistance.*—Neither resistance nor susceptibility to normal diseases and pests of *Abelia* have been observed.

*Temperature tolerance.*—Typical range USDA zones 5 through 9.

What is claimed is:

1. A new and distinct cultivar of *Abelia* plant named 'LITTLE LADY' as herein illustrated and described.

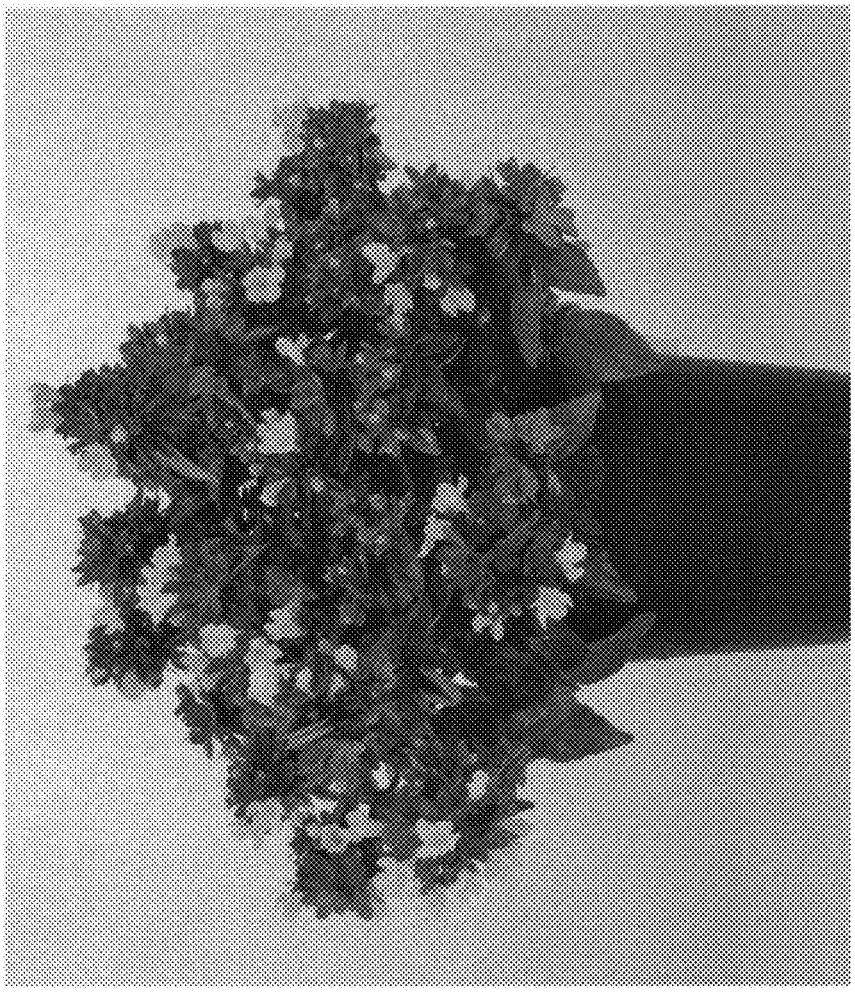

* * * * *